(12) United States Patent
Kellner et al.

(10) Patent No.: US 7,432,348 B2
(45) Date of Patent: Oct. 7, 2008

(54) 180 KD PROTEIN THAT INTERACTS WITH PROTEIN HISTIDINE PHOSPHATASE 1

(75) Inventors: Roland Kellner, Heppenheim (DE); Bjoern Hock, Maintal (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 10/483,679

(22) PCT Filed: Jul. 11, 2002

(86) PCT No.: PCT/EP02/07728

§ 371 (c)(1),
(2), (4) Date: Jan. 13, 2004

(87) PCT Pub. No.: WO03/006493

PCT Pub. Date: Jan. 23, 2003

(65) Prior Publication Data

US 2004/0265818 A1 Dec. 30, 2004

(30) Foreign Application Priority Data

Jul. 13, 2001 (EP) .................. 01116640

(51) Int. Cl.
*C07K 14/435* (2006.01)
*C12N 9/16* (2006.01)

(52) U.S. Cl. ...................... 530/350; 435/196
(58) Field of Classification Search .............. 530/350; 435/196

See application file for complete search history.

(56) References Cited

U.S. PATENT DOCUMENTS

2003/0212257 A1 * 11/2003 Spytek et al. ............... 530/350

FOREIGN PATENT DOCUMENTS

WO    WO 02081629    10/2002

OTHER PUBLICATIONS

Revised Interim Written Description Guidelines Training Materials, http://www.uspto.gov/web/offices/pac/writtendesc. pdf, pp. 27-29, printed on Oct. 17, 2006.*
Nagase T et al., "Prediction of the coding sequences of unidentified human genes. XVI. The complete sequences of 150 new cDNA clones from brain which code for large proteins in vitro," DNA Research 2000, pp. 65-73, vol. 7, XP000923011, The DNA and polypeptide sequences of KIAA1365 comprise the sequences of SEQ IDs No. 1 and 2 repectively, abstract.
Apperson Michelle L II Soo Moon et al., "Characterization of densin-180, a new brain-specific synaptic protein of the O-sialoglycoprotein family," Journal of Neuroscience, 1996, pp. 6839-6852, vol. 16, No. 21, XP002247309, ISSN: 0270-6474, abstract.
Strack Stefan et al., "Association of calcium/calmodulin-dependent kinase II with developmentally regulated splice variants of the postsynaptic density protein densin-180," Journal of Biological Chemistry, Aug. 18, 2000, pp. 25061-25064, vol. 275, No. 33, ISSN: 0021-9258, abstract.
Walikonis Randall S et al., "Densin-180 forms a temary complex with the alpha-subunit of Ca2+/calmodulin-dependent protein kinase II and alpha-actinin," Journal of Neuroscience, Jan. 15, 2001, pp. 423-433, vol. 21, No. 2, XP002247311, ISSN: 0270-6474, the whole document.
Izawa Ichiro et al., "Densin-180 interacts with delta-catenin/neural plakophilin-related armadillo repeat protein at synapses," Journal of Biological Chemistry, Feb. 15, 2002, pp. 5345-5350, vol. 277, No. 7, XP002247312, ISSN: 0021-9258, the whole document.

* cited by examiner

*Primary Examiner*—Rebecca E. Prouty
*Assistant Examiner*—Rosanne Kosson
(74) *Attorney, Agent, or Firm*—Millen, White, Zelano, Branigan, P.C.

(57) ABSTRACT

180 KDa protein histidine phosphatase interacting protein (PHPIP-180) polypeptides and polynucleotides and methods for producing such polypeptides by recombinant techniques are disclosed. Also disclosed are methods for utilizing PHPIP-180 polypeptides and polynucleotides in diagnostic assays.

4 Claims, No Drawings

SEQUENCE LISTING

<160> NUMBER OF SEQ ID NOS: 8

<210> SEQ ID NO 1
<211> LENGTH: 3312

```
<212> TYPE: DNA
<213> ORGANISM: Homo sapiens
<220> FEATURE:
<221> NAME/KEY: CDS
<222> LOCATION: (3)..(1715)

<400> SEQUENCE: 1 ct aaa ggt gtt att tca att agc aaa agc aca gag agg ctt tcc ccc        47
   Lys Gly Val Ile Ser Ile Ser Lys Ser Thr Glu Arg Leu Ser Pro
   1               5                   10                  15 cta atg aaa gat atc aag tct aat aaa ttc aaa aag tca cag agt atc       95
Leu Met Lys Asp Ile Lys Ser Asn Lys Phe Lys Lys Ser Gln Ser Ile
            20                  25                  30 gat gag att gac att ggt aca tat aag gtg tat aac ata cca tta gaa      143
Asp Glu Ile Asp Ile Gly Thr Tyr Lys Val Tyr Asn Ile Pro Leu Glu
        35                  40                  45 aac tat gct tct ggg agt gat cac tta gga agc cac gaa cga ccg gat      191
Asn Tyr Ala Ser Gly Ser Asp His Leu Gly Ser His Glu Arg Pro Asp
    50                  55                  60 aag atg ctg gga cca gag cat ggt atg tcc agt atg tct cga agc cag      239
Lys Met Leu Gly Pro Glu His Gly Met Ser Ser Met Ser Arg Ser Gln
65                  70                  75 tca gtc cca atg ctg gat gat gag atg ctc acc tac gga agt agt aag      287
Ser Val Pro Met Leu Asp Asp Glu Met Leu Thr Tyr Gly Ser Ser Lys
 80                  85                  90                  95 ggg cca caa caa caa aaa gct tct atg aca aaa aaa gtc tat cag ttt      335
Gly Pro Gln Gln Gln Lys Ala Ser Met Thr Lys Lys Val Tyr Gln Phe
                100                 105                 110 gac caa agc ttc aat cct caa gga tca gtg gaa gtg aaa gcc gaa aag      383
Asp Gln Ser Phe Asn Pro Gln Gly Ser Val Glu Val Lys Ala Glu Lys
            115                 120                 125 agg ata cca ccc cct ttt caa cac aat ccc gag tac gtg caa cag gcc      431
Arg Ile Pro Pro Pro Phe Gln His Asn Pro Glu Tyr Val Gln Gln Ala
        130                 135                 140 agc aaa aac atc gcc aag gat ttg att agt cct aga gct tac aga gga      479
Ser Lys Asn Ile Ala Lys Asp Leu Ile Ser Pro Arg Ala Tyr Arg Gly
    145                 150                 155 tac cca ccg atg gag caa atg ttt tca ttt tct cag cca tct gtg aat      527
Tyr Pro Pro Met Glu Gln Met Phe Ser Phe Ser Gln Pro Ser Val Asn
160                 165                 170                 175 gag gat gct gtg gtg aat gcc cag ttc gca agc caa ggg gcc agg gcg      575
Glu Asp Ala Val Val Asn Ala Gln Phe Ala Ser Gln Gly Ala Arg Ala
                180                 185                 190 ggc ttc ctg aga agg gcc gac tcc ctg gtg agc gcc aca gaa atg gcc      623
Gly Phe Leu Arg Arg Ala Asp Ser Leu Val Ser Ala Thr Glu Met Ala
            195                 200                 205 atg ttt aga agg gtc aat gag cct cat gag ctg ccc cca act gat agg      671
Met Phe Arg Arg Val Asn Glu Pro His Glu Leu Pro Pro Thr Asp Arg
        210                 215                 220 tac ggc aga ccc cca tat agg gga ggg ctg gat cgc caa agc agc gtt      719
Tyr Gly Arg Pro Pro Tyr Arg Gly Gly Leu Asp Arg Gln Ser Ser Val
    225                 230                 235 aca gtg act gag tcc cag ttc ctg aaa agg aat ggc agg tat gaa gat      767
Thr Val Thr Glu Ser Gln Phe Leu Lys Arg Asn Gly Arg Tyr Glu Asp
240                 245                 250                 255 gaa cac cct tca tat caa gaa gtg aaa gct cag gcg gga agt ttt ccg      815
Glu His Pro Ser Tyr Gln Glu Val Lys Ala Gln Ala Gly Ser Phe Pro
                260                 265                 270 gtt aaa aac ctt acc caa agg agg cca ttg tct gcg aga agc tac agt      863
Val Lys Asn Leu Thr Gln Arg Arg Pro Leu Ser Ala Arg Ser Tyr Ser
            275                 280                 285
```

```
aca gag agt tac ggt gcc tcc caa acc agg cca gtt tca gct agg cct       911
Thr Glu Ser Tyr Gly Ala Ser Gln Thr Arg Pro Val Ser Ala Arg Pro
        290                 295                 300 act atg gca gct ctt ttg gaa aaa ata cca tct gac tat aac ttg ggt       959
Thr Met Ala Ala Leu Leu Glu Lys Ile Pro Ser Asp Tyr Asn Leu Gly
305                 310                 315 aac tat ggt gac aag cca tca gat aac agt gat tta aag acg agg cct      1007
Asn Tyr Gly Asp Lys Pro Ser Asp Asn Ser Asp Leu Lys Thr Arg Pro
320                 325                 330                 335 act cct gtg aag gga gag gag agc tgt ggt aaa atg cct gca gac tgg      1055
Thr Pro Val Lys Gly Glu Glu Ser Cys Gly Lys Met Pro Ala Asp Trp
                340                 345                 350 aga caa cag ctg ctt aga cat ata gaa gct aga cgg tta gac agg acc      1103
Arg Gln Gln Leu Leu Arg His Ile Glu Ala Arg Arg Leu Asp Arg Thr
            355                 360                 365 ccg tcc cag caa agc aac att tta gac aat gga caa gaa gat gta tct      1151
Pro Ser Gln Gln Ser Asn Ile Leu Asp Asn Gly Gln Glu Asp Val Ser
        370                 375                 380 cct agt ggc caa tgg aat cct tat cca ctt ggg agg cgg gat gta cct      1199
Pro Ser Gly Gln Trp Asn Pro Tyr Pro Leu Gly Arg Arg Asp Val Pro
385                 390                 395 ccg gac acc att act aag aag gca ggc agc cac atc cag acg ttg atg      1247
Pro Asp Thr Ile Thr Lys Lys Ala Gly Ser His Ile Gln Thr Leu Met
400                 405                 410                 415 ggg tcc caa agc ctt cag cat cgc agc cgg gag cag cag ccg tat gaa      1295
Gly Ser Gln Ser Leu Gln His Arg Ser Arg Glu Gln Gln Pro Tyr Glu
                420                 425                 430 gga aat ata aac aaa gtg acc atc cag caa ttt cag tca cca ttg cct      1343
Gly Asn Ile Asn Lys Val Thr Ile Gln Gln Phe Gln Ser Pro Leu Pro
            435                 440                 445 att cag atc ccc tct tca cag gcc acc cgg gga cct cag cct gga cgg      1391
Ile Gln Ile Pro Ser Ser Gln Ala Thr Arg Gly Pro Gln Pro Gly Arg
        450                 455                 460 tgc tta att caa act aaa ggg caa agg agt atg gat gga tat cca gag      1439
Cys Leu Ile Gln Thr Lys Gly Gln Arg Ser Met Asp Gly Tyr Pro Glu
465                 470                 475 cag ttt tgt gtg aga ata gaa aag aat cct ggc ctt gga ttt agt atc      1487
Gln Phe Cys Val Arg Ile Glu Lys Asn Pro Gly Leu Gly Phe Ser Ile
480                 485                 490                 495 agt ggt gga att agt gga caa gga aat cca ttc aaa cct tct gac aag      1535
Ser Gly Gly Ile Ser Gly Gln Gly Asn Pro Phe Lys Pro Ser Asp Lys
                500                 505                 510 ggt atc ttt gtt act agg gtt cag cct gat ggg cca gca tca aac cta      1583
Gly Ile Phe Val Thr Arg Val Gln Pro Asp Gly Pro Ala Ser Asn Leu
            515                 520                 525 ctg cag cct ggt gat aag atc ctt cag gca aat gga cac agt ttt gta      1631
Leu Gln Pro Gly Asp Lys Ile Leu Gln Ala Asn Gly His Ser Phe Val
        530                 535                 540 cat atg gaa cat gaa aaa gct gta tta cta ctg aag agt ttc cag aac      1679
His Met Glu His Glu Lys Ala Val Leu Leu Leu Lys Ser Phe Gln Asn
545                 550                 555 aca gta gac cta gtt att caa cgt gag ctt act gtc taaatatttt           1725
Thr Val Asp Leu Val Ile Gln Arg Glu Leu Thr Val
560                 565                 570 ttataaatag tgaagatacg tctagccaga cctaatgttc aaaataaat ttatacatag     1785 aaacaaattt tgccaattgc tggaccaatg gcaaacatta gtgccaaatg tataatacta    1845
tatgttagca ctgaccatcc ttaaaaaatg ttaactctat aaatatgatg ttcatgtggt   1905
```

```
tatgtattag tttaattgt cagcctctgg ctgtgcattg gtgcagtttt gtttctgttt    1965
ttgtttttgt tttaatcaa ataagtttct tctcaaaatg gatttcatat aatttcggag    2025
cacggaagca cacacaagct ctttatgaat tctgctctcc atcagaaaca ctgcctcaaa    2085
gttgtatatg cctttatata gaaaatacaa atataaagaa ttgtaattcc cataaaatat    2145
ttctagcaca aggtatatgt tggcatatat acaaaaagaa tatagagaaa aacaatattt    2205
tcataaacta aacatctcag atagagaaaa aatatatctt aaaataagac tttactatat    2265
tgaatctttt tcaataaaaa ttacatgata atgccttatg aaagtaactg tacatatggt    2325
ataaagtgtt tatatttggt tccatattca tttgctaaat tctcatgaca cagagtgaaa    2385
tatttcataa attagccatt tatctctggg acccaaataa aaataggatg aactaatttg    2445
ttcaatgcct ttagctaatt acaatacatg cagagtttag aaacagacta aaggtcattg    2505
tagttaagtc ttttcacca caaatttaag cagtggatga tgggtggcag aaaggtatt     2565 gctttatttc tttcaagttc atgttgatta taaactgtag cccctgtgat ttctttactt    2625
gtaaatgtgg aatttatttg tgtgttgctt aatctaattt gctgctttt aaattattta    2685 aaacgaattt tggaaattga taaaatttat cattacgaaa gactgctgtt agaaagttat    2745
ggtaggtgat tttaaatcct tggtatttaa atatgaaact tcaaatataa tttctcagag    2805
ctgtggtcta cctgtatcat taatttcaat ggctgttttt ctgggcagaa atagataaaa    2865 tactttttt ccaaaaacag tttcaaggta tgtaaaatcc tgaatgcttt ttcactgaag     2925
agaaagacaa gcatggttaa tgtagaatta tttactttc cattgaaact atttcctgc     2985 ataaatgatc aaaatttatt ttataatcct ttaaaatact tatctttcat attagtcatt    3045
aatttaatta caatattaat ttgaatttcc aggataattt cccggagttg gttgcatgca    3105
ttatctttca taatttaca tagttctttt gttatataat gaatttactt tacatgctag     3165
tgtttcaagt attgtatgag gattttcaca atagtatcac tgaatgatgt caccagagct    3225
ctgagaataa tatttgtaag ttaactgttt tatggggaca ttgaaaatat tgtatttttg    3285
tagggtctat taaatgagt gtcactt                                         3312
```

<210> SEQ ID NO 2
<211> LENGTH: 571
<212> TYPE: PRT
<213> ORGANISM: Homo sapiens

<400> SEQUENCE: 2

Lys Gly Val Ile Ser Ile Ser Lys Ser Thr Glu Arg Leu Ser Pro Leu
 1               5                  10                  15

Met Lys Asp Ile Lys Ser Asn Lys Phe Lys Lys Ser Gln Ser Ile Asp
            20                  25                  30

Glu Ile Asp Ile Gly Thr Tyr Lys Val Tyr Asn Ile Pro Leu Glu Asn
        35                  40                  45

Tyr Ala Ser Gly Ser Asp His Leu Gly Ser His Glu Arg Pro Asp Lys
    50                  55                  60

Met Leu Gly Pro Glu His Gly Met Ser Ser Met Ser Arg Ser Gln Ser
65                  70                  75                  80

Val Pro Met Leu Asp Asp Glu Met Leu Thr Tyr Gly Ser Ser Lys Gly
                85                  90                  95

Pro Gln Gln Gln Lys Ala Ser Met Thr Lys Lys Val Tyr Gln Phe Asp
            100                 105                 110

Gln Ser Phe Asn Pro Gln Gly Ser Val Glu Val Lys Ala Glu Lys Arg
        115                 120                 125

```
Ile Pro Pro Pro Phe Gln His Asn Pro Glu Tyr Val Gln Gln Ala Ser
    130                 135                 140

Lys Asn Ile Ala Lys Asp Leu Ile Ser Pro Arg Ala Tyr Arg Gly Tyr
145                 150                 155                 160

Pro Pro Met Glu Gln Met Phe Ser Phe Ser Gln Pro Ser Val Asn Glu
                165                 170                 175

Asp Ala Val Val Asn Ala Gln Phe Ala Ser Gln Gly Ala Arg Ala Gly
            180                 185                 190

Phe Leu Arg Arg Ala Asp Ser Leu Val Ser Ala Thr Glu Met Ala Met
        195                 200                 205

Phe Arg Arg Val Asn Glu Pro His Glu Leu Pro Pro Thr Asp Arg Tyr
    210                 215                 220

Gly Arg Pro Pro Tyr Arg Gly Gly Leu Asp Arg Gln Ser Ser Val Thr
225                 230                 235                 240

Val Thr Glu Ser Gln Phe Leu Lys Arg Asn Gly Arg Tyr Glu Asp Glu
                245                 250                 255

His Pro Ser Tyr Gln Glu Val Lys Ala Gln Ala Gly Ser Phe Pro Val
            260                 265                 270

Lys Asn Leu Thr Gln Arg Arg Pro Leu Ser Ala Arg Ser Tyr Ser Thr
        275                 280                 285

Glu Ser Tyr Gly Ala Ser Gln Thr Arg Pro Val Ser Ala Arg Pro Thr
    290                 295                 300

Met Ala Ala Leu Leu Glu Lys Ile Pro Ser Asp Tyr Asn Leu Gly Asn
305                 310                 315                 320

Tyr Gly Asp Lys Pro Ser Asp Asn Ser Asp Leu Lys Thr Arg Pro Thr
                325                 330                 335

Pro Val Lys Gly Glu Glu Ser Cys Gly Lys Met Pro Ala Asp Trp Arg
            340                 345                 350

Gln Gln Leu Leu Arg His Ile Glu Ala Arg Arg Leu Asp Arg Thr Pro
        355                 360                 365

Ser Gln Gln Ser Asn Ile Leu Asp Asn Gly Gln Glu Asp Val Ser Pro
    370                 375                 380

Ser Gly Gln Trp Asn Pro Tyr Pro Leu Gly Arg Arg Asp Val Pro Pro
385                 390                 395                 400

Asp Thr Ile Thr Lys Lys Ala Gly Ser His Ile Gln Thr Leu Met Gly
                405                 410                 415

Ser Gln Ser Leu Gln His Arg Ser Arg Glu Gln Gln Pro Tyr Glu Gly
            420                 425                 430

Asn Ile Asn Lys Val Thr Ile Gln Gln Phe Gln Ser Pro Leu Pro Ile
        435                 440                 445

Gln Ile Pro Ser Ser Gln Ala Thr Arg Gly Pro Gln Pro Gly Arg Cys
    450                 455                 460

Leu Ile Gln Thr Lys Gly Gln Arg Ser Met Asp Gly Tyr Pro Glu Gln
465                 470                 475                 480

Phe Cys Val Arg Ile Glu Lys Asn Pro Gly Leu Gly Phe Ser Ile Ser
                485                 490                 495

Gly Gly Ile Ser Gly Gln Gly Asn Pro Phe Lys Pro Ser Asp Lys Gly
            500                 505                 510

Ile Phe Val Thr Arg Val Gln Pro Asp Gly Pro Ala Ser Asn Leu Leu
        515                 520                 525

Gln Pro Gly Asp Lys Ile Leu Gln Ala Asn Gly His Ser Phe Val His
    530                 535                 540
```

```
Met Glu His Glu Lys Ala Val Leu Leu Lys Ser Phe Gln Asn Thr
545                 550                 555                 560

Val Asp Leu Val Ile Gln Arg Glu Leu Thr Val
                565                 570

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Primer 1

<400> SEQUENCE: 3
ttttgtcgac catggcggtg gcggacctcg                                        30

<210> SEQ ID NO 4
<211> LENGTH: 31
<212> TYPE: DNA
<213> ORGANISM: Artificial Sequence
<220> FEATURE:
<223> OTHER INFORMATION: Description of Artificial Sequence: Primer 2

<400> SEQUENCE: 4
ttttgcggcc gctcagtagc cgtcgttagc c                                      31

<210> SEQ ID NO 5
<211> LENGTH: 29
<212> TYPE: DNA
<213> ORGANISM: Artificial Sequence
<220> FEATURE:
<223> OTHER INFORMATION: Description of Artificial Sequence: Primer 3

<400> SEQUENCE: 5
aattccaggt cgacctcgag gcggccgct                                         29

<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence: Primer 4

<400> SEQUENCE: 6
tcgaaccggc cgcctcgagg tcgacctgg                                         29

<210> SEQ ID NO 7
<211> LENGTH: 276
<212> TYPE: PRT
<213> ORGANISM: Artificial Sequence
<220> FEATURE:
<223> OTHER INFORMATION: Description of Artificial Sequence:
      Fusionprotein
      Gal-4 PHP1

<400> SEQUENCE: 7

Met Lys Leu Leu Ser Ser Ile Glu Gln Ala Cys Asp Ile Cys Arg Leu
 1               5                  10                  15

Lys Lys Leu Lys Cys Ser Lys Glu Lys Pro Lys Cys Ala Lys Cys Leu
                20                  25                  30

Lys Asn Asn Trp Glu Cys Arg Tyr Ser Pro Lys Thr Lys Arg Ser Pro
            35                  40                  45

Leu Thr Arg Ala His Leu Thr Glu Val Glu Ser Arg Leu Glu Arg Leu
        50                  55                  60

Glu Gln Leu Phe Leu Leu Ile Phe Pro Arg Glu Asp Leu Asp Met Ile
```

```
                65                  70                  75                  80
Leu Lys Met Asp Ser Leu Gln Asp Ile Lys Ala Leu Leu Thr Gly Leu
                    85                  90                  95

Phe Val Gln Asp Asn Val Asn Lys Asp Ala Val Thr Asp Arg Leu Ala
                100                 105                 110

Ser Val Glu Thr Asp Met Pro Leu Thr Leu Arg Gln His Arg Ile Ser
                115                 120                 125

Ala Thr Ser Ser Ser Glu Glu Ser Ser Asn Lys Gly Gln Arg Gln Leu
            130                 135                 140

Thr Val Ser Ser Arg Ser Thr Met Ala Val Ala Asp Leu Ala Leu Ile
145                 150                 155                 160

Pro Asp Val Asp Ile Asp Ser Asp Gly Val Phe Lys Tyr Val Leu Ile
                165                 170                 175

Arg Val His Ser Ala Pro Arg Ser Gly Ala Pro Ala Ala Glu Ser Lys
                180                 185                 190

Glu Ile Val Arg Gly Tyr Lys Trp Ala Glu Tyr His Ala Asp Ile Tyr
            195                 200                 205

Asp Lys Val Ser Gly Asp Met Gln Lys Gln Gly Cys Asp Cys Glu Cys
210                 215                 220

Leu Gly Gly Gly Arg Ile Ser His Gln Ser Gln Asp Lys Lys Ile His
225                 230                 235                 240

Val Tyr Gly Tyr Ser Met Ala Tyr Gly Pro Ala Gln His Ala Ile Ser
                245                 250                 255

Thr Glu Lys Ile Lys Ala Lys Tyr Pro Asp Tyr Glu Val Thr Trp Ala
            260                 265                 270

Asn Asp Gly Tyr
        275

<210> SEQ ID NO 8
<211> LENGTH: 332
<212> TYPE: PRT
<213> ORGANISM: Artificial Sequence
<220> FEATURE:
<223> OTHER INFORMATION: Description of Artificial Sequence:
      Fusionprotein
      LexA-PHP1

<400> SEQUENCE: 8

Met Lys Ala Leu Thr Ala Arg Gln Gln Glu Val Phe Asp Leu Ile Arg
  1               5                  10                  15

Asp His Ile Ser Gln Thr Gly Met Pro Pro Thr Arg Ala Glu Ile Ala
                20                  25                  30

Gln Arg Leu Gly Phe Arg Ser Pro Asn Ala Ala Glu Glu His Leu Lys
            35                  40                  45

Ala Leu Ala Arg Lys Gly Val Ile Glu Ile Val Ser Gly Ala Ser Arg
        50                  55                  60

Gly Ile Arg Leu Leu Gln Glu Glu Glu Gly Leu Pro Leu Val Gly
 65                 70                  75                  80

Arg Val Ala Ala Gly Glu Pro Leu Leu Ala Gln Gln His Ile Glu Gly
                85                  90                  95

His Tyr Gln Val Asp Pro Ser Leu Phe Lys Pro Asn Ala Asp Phe Leu
                100                 105                 110

Leu Arg Val Ser Gly Met Ser Met Lys Asp Ile Gly Ile Met Asp Gly
            115                 120                 125

Asp Leu Leu Ala Val His Lys Thr Gln Asp Val Arg Asn Gly Gln Val
        130                 135                 140
```

-continued

```
Val Val Ala Arg Ile Asp Asp Glu Val Thr Val Lys Arg Leu Lys Lys
145                 150                 155                 160

Gln Gly Asn Lys Val Glu Leu Leu Pro Glu Asn Ser Glu Phe Lys Pro
                165                 170                 175

Ile Val Val Asp Leu Arg Gln Gln Ser Phe Thr Ile Glu Gly Leu Ala
                180                 185                 190

Val Gly Val Ile Arg Asn Gly Asp Trp Leu Glu Phe Arg Ser Thr Met
            195                 200                 205

Ala Val Ala Asp Leu Ala Leu Ile Pro Asp Val Asp Ile Asp Ser Asp
        210                 215                 220

Gly Val Phe Lys Tyr Val Leu Ile Arg Val His Ser Ala Pro Arg Ser
225                 230                 235                 240

Gly Ala Pro Ala Ala Glu Ser Lys Glu Ile Val Arg Gly Tyr Lys Trp
                245                 250                 255

Ala Glu Tyr His Ala Asp Ile Tyr Asp Lys Val Ser Gly Asp Met Gln
            260                 265                 270

Lys Gln Gly Cys Asp Cys Glu Cys Leu Gly Gly Gly Arg Ile Ser His
        275                 280                 285

Gln Ser Gln Asp Lys Lys Ile His Val Tyr Gly Tyr Ser Met Ala Tyr
    290                 295                 300

Gly Pro Ala Gln His Ala Ile Ser Thr Glu Lys Ile Lys Ala Lys Tyr
305                 310                 315                 320

Pro Asp Tyr Glu Val Thr Trp Ala Asn Asp Gly Tyr
                325                 330
```

180 KD PROTEIN THAT INTERACTS WITH PROTEIN HISTIDINE PHOSPHATASE 1

This application is the U.S. national phase of International Application No. PCT/EP02/07728, filed on Jul. 11, 2002, which claims priority to European Application No. 01116640.2, filed on Jul. 13, 2001.

FIELD OF THE INVENTION

This invention relates to newly identified polypeptides and polynucleotides encoding such polypeptides sometimes hereinafter referred to as "novel Protein Histidine Phosphatase Interacting Partner of 180 KD (PHPIP-180)", to their use in diagnosis and in identifying compounds that may be agonists, antagonists that are potentially useful in therapy, and to production of such polypeptides and polynucleotides.

BACKGROUND OF THE INVENTION

Functional genomics relies heavily on high-throughput and the various tools of bioinformatics to identify gene sequences of potential interest from the many molecular biology databases now available. There is a continuing need to identify and characterise further genes and their related polypeptides/proteins, as targets for drug discovery.

Recently, the first human protein histidine phosphatase (PHP1) has been identified (Apperson et al.: J. Neurosci. 16: p6839, 1996). The enzyme was isolated from rabbit liver extracts and characterized. In human cell lines PHP1 is displayed in the cytoplasma. Functional studies with the orthologue protein in *C. elegans* showed a neuronal localization (Kennedy et al.: Trends Biochem. Sci, 20: p350, 1995) (Kennedy et al.: Trends Neurosci, 20: p264, 1997) (Kennedy et al.: Brain Res. Brain Res. Rev, 26: p243, 1998) (Kennedy et al.: Science, 290: p750, 2000) (Kornau et al.: Curr. Opin. Neurobiol, 7: p368, 1997). The *C. elegans* homologue of PHP1 has been localized in motor- and pharyngeal sensorineurons MC, M3 and 12. The analogy from a nematode's pharynx to the human heart is described (PNAS 95,5072-5, 1998) thus, PHP1 and ligand could be relevant for various cardiovascular diseases. PHP1 is furthermore expressed in skeletal muscle, kidney, liver and brain. Additional references referring to PHP1 includes (Omkumar et al.: J. Biol. Chem, 271: p31670, 1996) (Ouyang et al.: J. Neurosci, 19: p7823, 1999) (Walikonis et al.: J. Neurosci, 20: p4069, 2000) (Walikonis et al.: J. Neurosci, 21: p423, 2001) (Zang et al.: J. Neurosci, 19: p96, 1999. (Legouis et al.: Nature Cell Biol, 2: p415, 2000)

In the current application protein interaction studies with PHP1 have been used in combination with DNA sequencing technologies and bioinformatics to identify gene sequences and gene functions that are ligands and interaction partners of PHP-1 on a molecular level.

SUMMARY OF THE INVENTION

Protein interaction studies with PHP1 identified the PHPIP-180 as a yet unknown interaction partner.

The present invention relates to PHPIP-180, in particular PHPIP-180 polypeptides and PHPIP-180 polynucleotides, recombinant materials and methods for their production. Such polypeptides and polynucleotides are of interest in relation to methods of treatment of certain diseases, including, but not limited to various cardiovascular diseases furthermore autismus: a defect in nerve cells membrane activity linked to the fatty acid metabolim (Am J. Med. Genet. 4;96(6):765, 2000), schizophrenia (Psychiatr Q Winter; 65:287, 1994), familial recurrent arthritis (Arthritis Rheum; 43:2041, 2000), Bardet-Biedl Syndrome (BBS4) (Genomics; 41:93, 1997), congenital dyserythropoietic anemia type III (Haematologica 85,753, 2000), and Malignant fibrous histocytomas hereinafter referred to as "diseases of the invention". In a further aspect, the invention relates to methods for identifying agonists and antagonists (e.g., inhibitors) using the materials provided by the invention, and treating conditions associated with PHPIP-180 imbalance with the identified compounds. In a still further aspect, the invention relates to diagnostic assays for detecting diseases associated with inappropriate PHPIP-180 activity or levels.

DESCRIPTION OF THE INVENTION

In a first aspect, the present invention relates to PHPIP-180 polypeptides. Such polypeptides include:

(a) an isolated polypeptide encoded by a polynucleotide comprising the sequence of SEQ ID NO:1;
(b) an isolated polypeptide comprising a polypeptide sequence having at least 95%, 96%, 97%, 98%, or 99% identity to the polypeptide sequence of SEQ ID NO:2;
(c) an isolated polypeptide comprising the polypeptide sequence of SEQ ID NO:2;
(d) an isolated polypeptide having at least 95%, 96%, 97%, 98%, or 99% identity to the polypeptide sequence of SEQ ID NO:2;
(e) the polypeptide sequence of SEQ ID NO:2; and
(f) an isolated polypeptide having or comprising a polypeptide sequence that has an Identity Index of 0.95, 0.96, 0.97, 0.98, or 0.99 compared to the polypeptide sequence of SEQ ID NO:2;
(g) fragments and variants of such polypeptides in (a) to (f).

Polypeptides of the present invention are members of the PHPIP-180 family of polypeptides. PHPIP-180 is therefore of interest because they are ligands for human protein histidine phosphatase (PHP1). The human protein histidine phosphatase (PHP1) has been described recently (WO00/52175) and the characterization and comparison of said enzyme to protein isolated from rabbit liver extracts revealed that PHP1 was a specifically dephosphorylating ATP-citrate lyase, a key enzyme involved in the biosynthesis of acetylCoA and acetylcholine, and known to be phosporylated at position His-764. The substrate specificity identifies a role in the biosynthesis of fatty acids via preparation of acetylCoA. Accordingly, the biosynthesis of acetylcholine is regulated in nerve cells.

Hisitidine phosphorylation in mammals is involved in signal transduction via multimeric protein complexes. In human cell lines PHP1-ligands are displayed in the cytoplasma. Functional studies with the orthologue protein in *C. elegans* showed an exclusively neuronal localization, however other cell types outside that location do express it as well. Thus the new ligand is relevant for other diseases and especially for various cardiovascular disorders.

The PHPIP180-homologous protein LET-413 from *C. elegans* is described as a basolateral protein required for the assembly of adherens junctions (Legouis et al. Nature Cell Biol. 2000, 2:415). This suggests that let-413 acts as an adaptor protein involved in polarizing protein trafficking in epithelial cells. The biological properties of the PHPIP-180 are hereinafter referred to as "biological activity of PHPIP-180" or "PHPIP-180 activity". Preferably, a polypeptide of the present invention exhibits at least one biological activity of PHPIP-180.

Polypeptides of the present invention also includes variants of the aforementioned polypeptides, including all allelic forms and splice variants. Such polypeptides vary from the reference polypeptide by insertions, deletions, and substitutions that may be conservative or non-conservative, or any combination thereof. Particularly preferred variants are those in which several, for instance from 50 to 30, from 30 to 20, from 20 to 10, from 10 to 5, from 5 to 3, from 3 to 2, from 2 to 1 or 1 amino acids are inserted, substituted, or deleted, in any combination.

Preferred fragments of polypeptides of the present invention include an isolated polypeptide comprising an amino acid sequence having at least 30, 50 or 100 contiguous amino acids from the amino acid sequence of SEQ ID NO: 2, or an isolated polypeptide comprising an amino acid sequence having at least 30, 50 or 100 contiguous amino acids truncated or deleted from the amino acid sequence of SEQ ID NO: 2. Preferred fragments are biologically active fragments that mediate the biological activity of PHPIP-180, including those with a similar activity or an improved activity, or with a decreased undesirable activity. Also preferred are those fragments that are antigenic or immunogenic in an animal, especially in a human.

Fragments of the polypeptides of the invention may be employed for producing the corresponding full-length polypeptide by peptide synthesis; therefore, these variants may be employed as intermediates for producing the full-length polypeptides of the invention. The polypeptides of the present invention may be in the form of the "mature" protein or may be a part of a larger protein such as a precursor or a fusion protein. It is often advantageous to include an additional amino acid sequence that contains secretory or leader sequences, pro-sequences, sequences that aid in purification, for instance multiple histidine residues, or an additional sequence for stability during recombinant production.

Polypeptides of the present invention can be prepared in any suitable manner, for instance by isolation form naturally occurring sources, from genetically engineered host cells comprising expression systems (vide infra) or by chemical synthesis, using for instance automated peptide synthesizers, or a combination of such methods. Means for preparing such polypeptides are well understood in the art.

In a further aspect, the present invention relates to PHPIP-180 polynucleotides. Such polynucleotides include:

(a) an isolated polynucleotide comprising a polynucleotide sequence having at least 95%, 96%, 97%, 98%, or 99% identity to the polynucleotide sequence of SEQ ID NO:1;
(b) an isolated polynucleotide comprising the polynucleotide of SEQ ID NO:1;
(c) an isolated polynucleotide having at least 95%, 96%, 97%, 98%, or 99% identity to the polynucleotide of SEQ ID NO:1;
(d) the isolated polynucleotide of SEQ ID NO:1;
(e) an isolated polynucleotide comprising a polynucleotide sequence encoding a polypeptide sequence having at least 95%, 96%, 97%, 98%, or 99% identity to the polypeptide sequence of SEQ ID NO:2;
(f) an isolated polynucleotide comprising a polynucleotide sequence encoding the polypeptide of SEQ ID NO:2;
(g) an isolated polynucleotide having a polynucleotide sequence encoding a polypeptide sequence having at least 95%, 96%, 97%, 98%, or 99% identity to the polypeptide sequence of SEQ ID NO:2;
(h) an isolated polynucleotide encoding the polypeptide of SEQ ID NO:2;
(i) an isolated polynucleotide having or comprising a polynucleotide sequence that has an Identity Index of 0.95, 0.96, 0.97, 0.98, or 0.99 compared to the polynucleotide sequence of SEQ ID NO:1;
(j) an isolated polynucleotide having or comprising a polynucleotide sequence encoding a polypeptide sequence that has an Identity Index of 0.95, 0.96, 0.97, 0.98, or 0.99 compared to the polypeptide sequence of SEQ ID NO:2; and polynucleotides that are fragments and variants of the above mentioned polynucleotides or that are complementary to above mentioned polynucleotides, over the entire length thereof.

Preferred fragments of polynucleotides of the present invention include an isolated polynucleotide comprising an nucleotide sequence having at least 15, 30, 50 or 100 contiguous nucleotides from the sequence of SEQ ID NO: 1, or an isolated polynucleotide comprising an sequence having at least 30, 50 or 100 contiguous nucleotides truncated or deleted from the sequence of SEQ ID NO: 1.

Preferred variants of polynucleotides of the present invention include splice variants, allelic variants, and polymorphisms, including polynucleotides having one or more single nucleotide polymorphisms (SNPs).

Polynucleotides of the present invention also include polynucleotides encoding polypeptide variants that comprise the amino acid sequence of SEQ ID NO:2 and in which several, for instance from 50 to 30, from 30 to 20, from 20 to 10, from 10 to 5, from 5 to 3, from 3 to 2, from 2 to 1 or 1 amino acid residues are substituted, deleted or added, in any combination.

In a further aspect, the present invention provides polynucleotides that are RNA transcripts of the DNA sequences of the present invention. Accordingly, there is provided an RNA polynucleotide that:

(a) comprises an RNA transcript of the DNA sequence encoding the polypeptide of SEQ ID NO:2;
(b) is the RNA transcript of the DNA sequence encoding the polypeptide of SEQ ID NO:2;
(c) comprises an RNA transcript of the DNA sequence of SEQ ID NO:1; or
(d) is the RNA transcript of the DNA sequence of SEQ ID NO:1;

and RNA polynucleotides that are complementary thereto.

The polynucleotide sequence of SEQ ID NO:1 is a cDNA sequence that encodes the polypeptide of SEQ ID NO:2. The polynucleotide sequence encoding the polypeptide of SEQ ID NO:2 may be identical to the polypeptide encoding sequence of SEQ ID NO:1 or it may be a sequence other than SEQ ID NO:1, which, as a result of the redundancy (degeneracy) of the genetic code, also encodes the polypeptide of SEQ ID NO:2.

Preferred polypeptides and polynucleotides of the present invention are expected to have, inter alia, similar biological functions/properties to their homologous polypeptides and polynucleotides. Furthermore, preferred polypeptides and polynucleotides of the present invention have at least one PHPIP-180 activity.

Polynucleotides of the present invention may be obtained using standard cloning and screening techniques from a cDNA library derived from mRNA in cells of heart, skeletal muscle, liver, kidney, brain. However PHP1 might as well be isolated from other human tissues, where lower levels are found. The substrate specificity identifies a role in the biosynthesis of fatty acids via preparation of acetylCoA. Accordingly, the biosynthesis of acetylcholine is regulated in nerve cells.

(see for instance, Sambrook et al., Molecular Cloning: A Laboratory Manual, 2nd Ed., Cold Spring Harbor Laboratory Press, Cold Spring Harbor, N.Y. (1989)). Polynucleotides of the invention can also be obtained from natural sources such as genomic DNA libraries or can be synthesized using well known and commercially available techniques.

When polynucleotides of the present invention are used for the recombinant production of polypeptides of the present invention, the polynucleotide may include the coding sequence for the mature polypeptide, by itself, or the coding sequence for the mature polypeptide in reading frame with other coding sequences, such as those encoding a leader or secretory sequence, a pre-, or pro- or prepro-protein sequence, or other fusion peptide portions. For example, a marker sequence that facilitates purification of the fused polypeptide can be encoded. In certain preferred embodiments of this aspect of the invention, the marker sequence is a hexa-histidine peptide, as provided in the pQE vector (Qiagen, Inc.) and described in Gentz et al., Proc Natl Acad Sci USA (1989) 86:821-824, or is an HA tag. The polynucleotide may also contain non-coding 5' and 3' sequences, such as transcribed, non-translated sequences, splicing and polyadenylation signals, ribosome binding sites and sequences that stabilize mRNA.

Polynucleotides that are identical, or have sufficient identity to a polynucleotide sequence of SEQ ID NO:1, may be used as hybridization probes for cDNA and genomic DNA or as primers for a nucleic acid amplification reaction (for instance, PCR). Such probes and primers may be used to isolate full-length cDNAs and genomic clones encoding polypeptides of the present invention and to isolate cDNA and genomic clones of other genes (including genes encoding paralogs from human sources and orthologs and paralogs from species other than human) that have a high sequence similarity to SEQ ID NO:1, typically at least 95% identity. Preferred probes and primers will generally comprise at least 15 nucleotides, preferably, at least 30 nucleotides and may have at least 50, if not at least 100 nucleotides. Particularly preferred probes will have between 30 and 50 nucleotides. Particularly preferred primers will have between 20 and 25 nucleotides.

A polynucleotide encoding a polypeptide of the present invention, including homologs from species other than human, may be obtained by a process comprising the steps of screening a library under stringent hybridization conditions with a labeled probe having the sequence of SEQ ID NO: 1 or a fragment thereof, preferably of at least 15 nucleotides; and isolating full-length cDNA and genomic clones containing said polynucleotide sequence: Such hybridization techniques are well known to the skilled artisan. Preferred stringent hybridization conditions include overnight incubation at 42° C. in a solution comprising: 50% formamide, 5×SSC (150 mM NaCl, 15 mM trisodium citrate), 50 mM sodium phosphate (pH 7.6), 5× Denhardt's solution, 10% dextran sulfate, and 20 microgram/ml denatured, sheared salmon sperm DNA; followed by washing the filters in 0.1×SSC at about 65° C. Thus the present invention also includes isolated polynucleotides, preferably with a nucleotide sequence of at least 100, obtained by screening a library under stringent hybridization conditions with a labeled probe having the sequence of SEQ ID NO:1 or a fragment thereof, preferably of at least 15 nucleotides.

The skilled artisan will appreciate that, in many cases, an isolated cDNA sequence will be incomplete, in that the region coding for the polypeptide does not extend all the way through to the 5' terminus. This is a consequence of reverse transcriptase, an enzyme with inherently low "processivity" (a measure of the ability of the enzyme to remain attached to the template during the polymerisation reaction), failing to complete a DNA copy of the mRNA template during first strand cDNA synthesis.

There are several methods available and well known to those skilled in the art to obtain full-length cDNAs, or extend short cDNAs, for example those based on the method of Rapid Amplification of cDNA ends (RACE) (see, for example, Frohman et al., Proc Nat Acad Sci USA 85, 8998-9002, 1988). Recent modifications of the technique, exemplified by the Marathon (trade mark) technology (Clontech Laboratories Inc.) for example, have significantly simplified the search for longer cDNAs. In the Marathon (trade mark) technology, cDNAs have been prepared from mRNA extracted from a chosen tissue and an 'adaptor' sequence ligated onto each end. Nucleic acid amplification (PCR) is then carried out to amplify the "missing" 5' end of the cDNA using a combination of gene specific and adaptor specific oligonucleotide primers. The PCR reaction is then repeated using 'nested' primers, that is, primers designed to anneal within the amplified product (typically an adapter specific primer that anneals further 3' in the adaptor sequence and a gene specific primer that anneals further 5' in the known gene sequence). The products of this reaction can then be analyzed by DNA sequencing and a full-length cDNA constructed either by joining the product directly to the existing cDNA to give a complete sequence, or carrying out a separate full-length PCR using the new sequence information for the design of the 5' primer.

Recombinant polypeptides of the present invention may be prepared by processes well known in the art from genetically engineered host cells comprising expression systems. Accordingly, in a further aspect, the present invention relates to expression systems comprising a polynucleotide or polynucleotides of the present invention, to host cells which are genetically engineered with such expression systems and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. Polynucleotides may be introduced into host cells by methods described in many standard laboratory manuals, such as Davis et al., Basic Methods in Molecular Biology (1986) and Sambrook et al.(ibid). Preferred methods of introducing polynucleotides into host cells include, for instance, calcium phosphate transfection, DEAE-dextran mediated transfection, transvection, micro-injection, cationic lipid-mediated transfection, electroporation, transduction, scrape loading, ballistic introduction or infection.

Representative examples of appropriate hosts include bacterial cells, such as *Streptococci*, *Staphylococci*, *E. coli*, *Streptomyces* and *Bacillus subtilis* cells; fungal cells, such as yeast cells and *Aspergillus* cells; insect cells such as *Drosophila* S2 and *Spodoptera* Sf9 cells; animal cells such as CHO, COS, HeLa, C127, 3T3, BHK, HEK 293 and Bowes melanoma cells; and plant cells.

A great variety of expression systems can be used, for instance, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector that is able to maintain, propagate or express a polynucleotide to produce a polypeptide in a host may be used. The appropriate polynucleotide sequence may be inserted into an expression system by any of a variety of well-known and routine techniques, such as, for example, those set forth in Sambrook et al., (ibid). Appropriate secretion signals may be incorporated into the desired polypeptide to allow secretion of the translated protein into the lumen of the endoplasmic reticulum, the periplasmic space or the extracellular environment. These signals may be endogenous to the polypeptide or they may be heterologous signals.

If a polypeptide of the present invention is to be expressed for use in screening assays, it is generally preferred that the polypeptide be produced at the surface of the cell. In this event, the cells may be harvested prior to use in the screening assay. If the polypeptide is secreted into the medium, the medium can be recovered in order to recover and purify the polypeptide. If produced intracellularly, the cells must first be lysed before the polypeptide is recovered.

Polypeptides of the present invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during intracellular synthesis, isolation and/or purification.

Polynucleotides of the present invention may be used as diagnostic reagents, through detecting mutations in the associated gene. Detection of a mutated form of the gene characterized by the polynucleotide of SEQ ID NO:1 in the cDNA or genomic sequence and which is associated with a dysfunction will provide a diagnostic tool that can add to, or define, a diagnosis of a disease, or susceptibility to a disease, which results from under-expression, over-expression or altered spatial or temporal expression of the gene. Individuals carrying mutations in the gene may be detected at the DNA level by a variety of techniques well known in the art.

Nucleic acids for diagnosis may be obtained from a subject's cells, such as from blood, urine, saliva, tissue biopsy or autopsy material. The genomic DNA may be used directly for detection or it may be amplified enzymatically by using PCR, preferably RT-PCR, or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled PHPIP-180 nucleotide sequences. Perfectly matched sequences can be distinguished from mismatched duplexes by RNase digestion or by differences in melting temperatures. DNA sequence difference may also be detected by alterations in the electrophoretic mobility of DNA fragments in gels, with or without denaturing agents, or by direct DNA sequencing (see, for instance, Myers et al., Science (1985) 230:1242). Sequence changes at specific locations may also be revealed by nuclease protection assays, such as RNase and S1 protection or the chemical cleavage method (see Cotton et al., Proc Natl Acad Sci USA (1985) 85: 4397-4401).

An array of oligonucleotides probes comprising PHPIP-180 polynucleotide sequence or fragments thereof can be constructed to conduct efficient screening of e.g., genetic mutations. Such arrays are preferably high density arrays or grids. Array technology methods are well known and have general applicability and can be used to address a variety of questions in molecular genetics including gene expression, genetic linkage, and genetic variability, see, for example, M. Chee et al., Science, 274, 610-613 (1996) and other references cited therein.

Detection of abnormally decreased or increased levels of polypeptide or mRNA expression may also be used for diagnosing or determining susceptibility of a subject to a disease of the invention. Decreased or increased expression can be measured at the RNA level using any of the methods well known in the art for the quantitation of polynucleotides, such as, for example, nucleic acid amplification, for instance PCR, RT-PCR, RNase protection, Northern blotting and other hybridization methods. Assay techniques that can be used to determine levels of a protein, such as a polypeptide of the present invention, in a sample derived from a host are well-known to those of skill in the art. Such assay methods include radio-immunoassays, competitive-binding assays, Western Blot analysis and ELISA assays.

Thus in another aspect, the present invention relates to a diagnostic kit comprising:
(a) a polynucleotide of the present invention, preferably the nucleotide sequence of SEQ ID NO: 1, or a fragment or an RNA transcript thereof;
(b) a nucleotide sequence complementary to that of (a);
(c) a polypeptide of the present invention, preferably the polypeptide of SEQ ID NO:2 or a fragment thereof; or
(d) an antibody to a polypeptide of the present invention, preferably to the polypeptide of SEQ ID NO:2.

It will be appreciated that in any such kit, (a), (b), (c) or (d) may comprise a substantial component. Such a kit will be of use in diagnosing a disease or susceptibility to a disease, particularly diseases of the invention, amongst others.

The polynucleotide sequences of the present invention are valuable for chromosome localisation studies. The sequence is specifically targeted to, and can hybridize with, a particular location on an individual human chromosome. The mapping of relevant sequences to chromosomes according to the present invention is an important first step in correlating those sequences with gene associated disease. Once a sequence has been mapped to a precise chromosomal location, the physical position of the sequence on the chromosome can be correlated with genetic map data. Such data are found in, for example, V. McKusick, Mendelian Inheritance in Man (available on-line through Johns Hopkins University Welch Medical Library). The relationship between genes and diseases that have been mapped to the same chromosomal region are then identified through linkage analysis (co-inheritance of physically adjacent genes). Precise human chromosomal localisations for a genomic sequence (gene fragment etc.) can be determined using Radiation Hybrid (RH) Mapping (Walter, M. Spillett, D., Thomas, P., Weissenbach, J., and Goodfellow, P., (1994) A method for constructing radiation hybrid maps of whole genomes, Nature Genetics 7, 22-28). A number of RH panels are available from Research Genetics (Huntsville, Ala., USA) e.g. the GeneBridge4 RH panel (Hum Mol Genet 1996 March;5(3):339-46 A radiation hybrid map of the human genome. Gyapay G, Schmitt K, Fizames C, Jones H, Vega-Czarny N, Spilleft D, Muselet D, Prud'Homme J F, Dib C, Auffray C, Morissette J, Weissenbach J, Goodfellow P N). To determine the chromosomal location of a gene using this panel, 93 PCRs are performed using primers designed from the gene of interest on RH DNAs. Each of these DNAs contains random human genomic fragments maintained in a hamster background (human/hamster hybrid cell lines). These PCRs result in 93 scores indicating the presence or absence of the PCR product of the gene of interest. These scores are compared with scores created using PCR products from genomic sequences of known location. This comparison is conducted at http://www.genome.wi.mit.edu/. The gene of the present invention maps to human chromosome 1p31.

The polynucleotide sequences of the present invention are also valuable tools for tissue expression studies. Such studies allow the determination of expression patterns of polynucleotides of the present invention which may give an indication as to the expression patterns of the encoded polypeptides in tissues, by detecting the mRNAs that encode them. The techniques used are well known in the art and include in situ hydridization techniques to clones arrayed on a grid, such as cDNA microarray hybridization (Schena et al, Science, 270, 467-470, 1995 and Shalon et al, Genome Res, 6, 639-645, 1996) and nucleotide amplification techniques such as PCR. A preferred method uses the TAQMAN (Trade mark) technology available from Perkin Elmer. Results from these studies can provide an indication of the normal function of the polypeptide in the organism. In addition, comparative studies of the normal expression pattern of mRNAs with that of mRNAs encoded by an alternative form of the same gene (for example, one having an alteration in polypeptide coding potential or a regulatory mutation) can provide valuable insights into the role of the polypeptides of the present invention, or that of inappropriate expression thereof in disease. Such inappropriate expression may be of a temporal, spatial or simply quantitative nature.

The polypeptides of the present invention are expressed in tissues of the heart, skeletal muscle, liver, kidney and brain.

A further aspect of the present invention relates to antibodies. The polypeptides of the invention or their fragments, or cells expressing them, can be used as immunogens to produce antibodies that are immunospecific for polypeptides of the present invention. The term "immunospecific" means that the antibodies have substantially greater affinity for the polypeptides of the invention than their affinity for other related polypeptides in the prior art.

Antibodies generated against polypeptides of the present invention may be obtained by administering the polypeptides or epitope-bearing fragments, or cells to an animal, preferably a non-human animal, using routine protocols. For preparation of monoclonal antibodies, any technique which provides antibodies produced by continuous cell line cultures can be used. Examples include the hybridoma technique (Kohler, G. and Milstein, C., Nature (1975) 256:495-497), the trioma technique, the human B-cell hybridoma technique (Kozbor et al., Immunology Today (1983) 4:72) and the EBV-hybridoma technique (Cole et al., Monoclonal Antibodies and Cancer Therapy, 77-96, Alan R. Liss, Inc., 1985).

Techniques for the production of single chain antibodies, such as those described in U.S. Pat. No. 4,946,778, can also be adapted to produce single chain antibodies to polypeptides of this invention. Also, transgenic mice, or other organisms, including other mammals, may be used to express humanized antibodies.

The above-described antibodies may be employed to isolate or to identify clones expressing the polypeptide or to purify the polypeptides by affinity chromatography. Antibodies against polypeptides of the present invention may also be employed to treat diseases of the invention, amongst others.

Polypeptides and polynucleotides of the present invention may also be used as vaccines. Accordingly, in a further aspect, the present invention relates to a method for inducing an immunological response in a mammal that comprises inoculating the mammal with a polypeptide of the present invention, adequate to produce antibody and/or T cell immune response, including, for example, cytokine-producing T cells or cytotoxic T cells, to protect said animal from disease, whether that disease is already established within the individual or not. An immunological response in a mammal may also be induced by a method comprises delivering a polypeptide of the present invention via a vector directing expression of the polynucleotide and coding for the polypeptide in vivo in order to induce such an immunological response to produce antibody to protect said animal from diseases of the invention. One way of administering the vector is by accelerating it into the desired cells as a coating on particles or otherwise. Such nucleic acid vector may comprise DNA, RNA, a modified nucleic acid, or a DNA/RNA hybrid. For use a vaccine, a polypeptide or a nucleic acid vector will be normally provided as a vaccine formulation (composition). The formulation may further comprise a suitable carrier. Since a polypeptide may be broken down in the stomach, it is preferably administered parenterally (for instance, subcutaneous, intramuscular, intravenous, or intra-dermal injection). Formulations suitable for parenteral administration include aqueous and non-aqueous sterile injection solutions that may contain anti-oxidants, buffers, bacteriostats and solutes that render the formulation instonic with the blood of the recipient; and aqueous and non-aqueous sterile suspensions that may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

Polypeptides of the present invention have one or more biological functions that are of relevance in one or more disease states, in particular the diseases of the invention hereinbefore mentioned. It is therefore useful to identify compounds that stimulate or inhibit the function or level of the polypeptide. Accordingly, in a further aspect, the present invention provides for a method of screening compounds to identify those that stimulate or inhibit the function or level of the polypeptide. Such methods identify agonists or antagonists that may be employed for therapeutic and prophylactic purposes for such diseases of the invention as hereinbefore mentioned. Compounds may be identified from a variety of sources, for example, cells, cell-free preparations, chemical libraries, collections of chemical compounds, and natural product mixtures. Such agonists or antagonists so-identified may be natural or modified substrates, ligands, receptors, enzymes, etc., as the case may be, of the polypeptide; a structural or functional mimetic thereof (see Coligan et al., Current Protocols in Immunology 1(2):Chapter 5 (1991)) or a small molecule. Such small molecules preferably have a molecular weight below 2,000 daltons, more preferably between 300 and 1,000 daltons, and most preferably between 400 and 700 daltons. It is preferred that these small molecules are organic molecules.

The screening method may simply measure the binding of a candidate compound to the polypeptide, or to cells or membranes bearing the polypeptide, or a fusion protein thereof, by means of a label directly or indirectly associated with the candidate compound. Alternatively, the screening method may involve measuring or detecting (qualitatively or quantitatively) the competitive binding of a candidate compound to the polypeptide against a labeled competitor (e.g. agonist or antagonist). Further, these screening methods may test whether the candidate compound results in a signal generated by activation or inhibition of the polypeptide, using detection systems appropriate to the cells bearing the polypeptide. Inhibitors of activation are generally assayed in the presence of a known agonist and the effect on activation by the agonist by the presence of the candidate compound is observed. Further, the screening methods may simply comprise the steps of mixing a candidate compound with a solution containing a polypeptide of the present invention, to form a mixture, measuring a PHPIP-180 activity in the mixture, and comparing the PHPIP-180 activity of the mixture to a control mixture which contains no candidate compound.

Polypeptides of the present invention may be employed in conventional low capacity screening methods and also in high-throughput screening (HTS) formats. Such HTS formats include not only the well-established use of 96- and, more recently, 384-well micotiter plates but also emerging methods such as the nanowell method described by Schullek et al, Anal Biochem., 246, 20-29, (1997).

Fusion proteins, such as those made from Fc portion and PHPIP-180 polypeptide, as hereinbefore described, can also be used for high-throughput screening assays to identify antagonists for the polypeptide of the present invention (see D. Bennett et al., J. Mol. Recognition, 8:52-58 (1995); and K. Johanson et al., J. Biol. Chem, 270(16):9459-9471 (1995)).

Screening Techniques

The polynucleotides, polypeptides and antibodies to the polypeptide of the present invention may also be used to configure screening methods for detecting the effect of added compounds on the production of mRNA and polypeptide in cells. For example, an ELISA assay may be constructed for measuring secreted or cell associated levels of polypeptide using monoclonal and polyclonal antibodies by standard methods known in the art. This can be used to discover agents that may inhibit or enhance the production of polypeptide (also called antagonist or agonist, respectively) from suitably manipulated cells or tissues.

A polypeptide of the present invention may be used to identify membrane bound or soluble receptors, if any, through standard receptor binding techniques known in the art. These include, but are not limited to, ligand binding and crosslinking assays in which the polypeptide is labeled with a radioactive isotope (for instance, $^{125}$I), chemically modified (for instance, biotinylated), or fused to a peptide sequence suitable for detection or purification, and incubated with a source of the putative receptor (cells, cell membranes, cell supernatants, tissue extracts, bodily fluids). Other methods include biophysical techniques such as surface plasmon resonance and spectroscopy. These screening methods may also be used to identify agonists and antagonists of the polypeptide that compete with the binding of the polypeptide to its receptors, if any. Standard methods for conducting such assays are well understood in the art.

Examples of antagonists of polypeptides of the present invention include antibodies or, in some cases, oligonucleotides or proteins that are closely related to the ligands, substrates, receptors, enzymes, etc., as the case may be, of the polypeptide, e.g., a fragment of the ligands, substrates, receptors, enzymes, etc.; or a small molecule that bind to the polypeptide of the present invention but do not elicit a response, so that the activity of the polypeptide is prevented.

Screening methods may also involve the use of transgenic technology and PHPIP-180 gene. The art of constructing transgenic animals is well established. For example, the PHPIP-180 gene may be introduced through microinjection into the male pronucleus of fertilized oocytes, retroviral transfer into pre- or post-implantation embryos, or injection of genetically modified, such as by electroporation, embryonic stem cells into host blastocysts. Particularly useful transgenic animals are so-called "knock-in" animals in which an animal gene is replaced by the human equivalent within the genome of that animal. Knock-in transgenic animals are useful in the drug discovery process, for target validation, where the compound is specific for the human target. Other useful transgenic animals are so-called "knock-out" animals in which the expression of the animal ortholog of a polypeptide of the present invention and encoded by an endogenous DNA sequence in a cell is partially or completely annulled. The gene knock-out may be targeted to specific cells or tissues, may occur only in certain cells or tissues as a consequence of the limitations of the technology, or may occur in all, or substantially all, cells in the animal. Transgenic animal technology also offers a whole animal expression-cloning system in which introduced genes are expressed to give large amounts of polypeptides of the present invention Screening kits for use in the above described methods form a further aspect of the present invention. Such screening kits comprise:

(a) a polypeptide of the present invention;
(b) a membrane expressing a polypeptide of the present invention; or
(d recombinant cell expressing a polypeptide of the present invention;
(c) a cell) an antibody to a polypeptide of the present invention;

polypeptide is preferably that of SEQ ID NO:2.

It which will be appreciated that in any such kit, (a), (b), (c) or (d) may comprise a substantial component.

Glossary

The following definitions are provided to facilitate understanding of certain terms used frequently hereinbefore.

"Antibodies" as used herein includes polyclonal and monoclonal antibodies, chimeric, single chain, and humanized antibodies, as well as Fab fragments, including the products of an Fab or other immunoglobulin expression library.

"Isolated" means altered "by the hand of man" from its natural state, i.e., if it occurs in nature, it has been changed or removed from its original environment, or both. For example, a polynucleotide or a polypeptide naturally present in a living organism is not "isolated," but the same polynucleotide or polypeptide separated from the coexisting materials of its natural state is "isolated", as the term is employed herein. Moreover, a polynucleotide or polypeptide that is introduced into an organism by transformation, genetic manipulation or by any other recombinant method is "isolated" even if it is still present in said organism, which organism may be living or non-living.

"Polynucleotide" generally refers to any polyribonucleotide (RNA) or polydeoxribonucleotide (DNA), which may be unmodified or modified RNA or DNA. "Polynucleotides" include, without limitation, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term "polynucleotide" also includes DNAs or RNAs containing one or more modified bases and DNAs or RNAs with backbones modified for stability or for other reasons. "Modified" bases include, for example, tritylated bases and unusual bases such as inosine. A variety of modifications may be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any polypeptide comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as post-translational processing, or by chemical modification techniques that are well known in the art. Such modifications are well described in basic texts and in more detailed monographs, as well as in a voluminous research literature. Modifications may occur anywhere in a polypeptide, including the peptide backbone, the amino acid side-chains and the amino or carboxyl termini. It will be appreciated that the same type of modification may be present to the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from post-translation natural processes or may be made by synthetic methods. Modifications include acetylation, acylation, ADP-ribosylation, amidation, biotinylation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination (see, for instance, Proteins—Structure and Molecular Properties, 2nd Ed., T. E. Creighton, W. H. Freeman and Company, New York, 1993; Wold, F., Post-translational Protein Modifications: Perspectives and Prospects, 1-12, in Post-translational Covalent Modification of Proteins, B. C. Johnson, Ed., Academic Press, New York, 1983; Seifter et al., "Analysis for protein modifications and nonprotein cofactors", Meth Enzymol, 182, 626-646, 1990, and Rattan et al., "Protein Synthesis: Post-translational Modifications and Aging", Ann NY Acad Sci, 663, 48-62, 1992).

"Fragment" of a polypeptide sequence refers to a polypeptide sequence that is shorter than the reference sequence but that retains essentially the same biological function or activity as the reference polypeptide. "Fragment" of a polynucleotide sequence refers to a polynucleotide sequence that is shorter than the reference sequence of SEQ ID NO:1.

"Variant" refers to a polynucleotide or polypeptide that differs from a reference polynucleotide or polypeptide, but retains the essential properties thereof. A typical variant of a polynucleotide differs in nucleotide sequence from the reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from the reference polypeptide. Generally, alterations are limited so that the sequences of the reference polypeptide and the variant are closely similar overall and, in many regions, identical. A variant and reference polypeptide may differ in amino acid sequence by one or more substitutions, insertions, deletions in any combination. A substituted or inserted amino acid residue may or may not be one encoded by the genetic code. Typical conservative substitutions include Gly, Ala; Val, Ile, Leu; Asp, Glu; Asn, Gln; Ser, Thr; Lys, Arg; and Phe and Tyr. A variant of a polynucleotide or polypeptide may be naturally occurring such as an allele, or it may be a variant that is not known to occur naturally. Non-naturally occurring variants of polynucleotides and polypeptides may be made by mutagenesis techniques or by direct synthesis. Also included as variants are polypeptides having one or more post-translational modifications, for instance glycosylation, phosphorylation, methylation, ADP ribosylation and the like. Embodiments include methylation of the N-terminal amino acid, phosphorylations of serines and threonines and modification of C-terminal glycines.

"Allele" refers to one of two or more alternative forms of a gene occurring at a given locus in the genome.

"Polymorphism" refers to a variation in nucleotide sequence (and encoded polypeptide sequence, if relevant) at a given position in the genome within a population.

"Single Nucleotide Polymorphism" (SNP) refers to the occurrence of nucleotide variability at a single nucleotide position in the genome, within a population. An SNP may occur within a gene or within intergenic regions of the genome. SNPs can be assayed using Allele Specific Amplification (ASA). For the process at least 3 primers are required. A common primer is used in reverse complement to the polymorphism being assayed. This common primer can be between 50 and 1500 bps from the polymorphic base. The other two (or more) primers are identical to each other except that the final 3' base wobbles to match one of the two (or more) alleles that make up the polymorphism. Two (or more) PCR reactions are then conducted on sample DNA, each using the common primer and one of the Allele Specific Primers.

"Splice Variant" as used herein refers to cDNA molecules produced from RNA molecules initially transcribed from the same genomic DNA sequence but which have undergone alternative RNA splicing. Alternative RNA splicing occurs when a primary RNA transcript undergoes splicing, generally for the removal of introns, which results in the production of more than one mRNA molecule each of that may encode different amino acid sequences. The term splice variant also refers to the proteins encoded by the above cDNA molecules.

"Identity" reflects a relationship between two or more polypeptide sequences or two or more polynucleotide sequences, determined by comparing the sequences. In general, identity refers to an exact nucleotide to nucleotide or amino acid to amino acid correspondence of the two polynucleotide or two polypeptide sequences, respectively, over the length of the sequences being compared.

"% Identity"—For sequences where there is not an exact correspondence, a "% identity" may be determined. In general, the two sequences to be compared are aligned to give a maximum correlation between the sequences. This may include inserting "gaps" in either one or both sequences, to enhance the degree of alignment. A % identity may be determined over the whole length of each of the sequences being compared (so-called global alignment), that is particularly suitable for sequences of the same or very similar length, or over shorter, defined lengths (so-called local alignment), that is more suitable for sequences of unequal length.

"Similarity" is a further, more sophisticated measure of the relationship between two polypeptide sequences. In general, "similarity" means a comparison between the amino acids of two polypeptide chains, on a residue by residue basis, taking into account not only exact correspondences between a between pairs of residues, one from each of the sequences being compared (as for identity) but also, where there is not an exact correspondence, whether, on an evolutionary basis, one residue is a likely substitute for the other. This likelihood has an associated "score" from which the "% similarity" of the two sequences can then be determined.

Methods for comparing the identity and similarity of two or more sequences are well known in the art. Thus for instance, programs available in the Wisconsin Sequence Analysis Package, version 9.1 (Devereux J et al, Nucleic Acids Res, 12, 387-395, 1984, available from Genetics Computer Group, Madison, Wis., USA), for example the programs BESTFIT and GAP, may be used to determine the % identity between two polynucleotides and the % identity and the % similarity between two polypeptide sequences. BESTFIT uses the "local homology" algorithm of Smith and Waterman (J Mol Biol, 147, 195-197, 1981, Advances in Applied Mathematics, 2, 482-489,1981) and finds the best single region of similarity between two sequences. BESTFIT is more suited to comparing two polynucleotide or two polypeptide sequences that are dissimilar in length, the program assuming that the shorter sequence represents a portion of the longer. In comparison, GAP aligns two sequences, finding a "maximum similarity", according to the algorithm of Neddleman and Wunsch (J Mol Biol, 48, 443-453, 1970). GAP is more suited to comparing sequences that are approximately the same length and an alignment is expected over the entire length. Preferably, the parameters "Gap Weight" and "Length Weight" used in each program are 50 and 3, for polynucleotide sequences and 12 and 4 for polypeptide sequences, respectively. Preferably, % identities and similarities are determined when the two sequences being compared are optimally aligned.

Other programs for determining identity and/or similarity between sequences are also known in the art, for instance the BLAST family of programs (Altschul S F et al, J Mol Biol, 215, 403-410, 1990, Altschul S F et al, Nucleic Acids Res., 25:389-3402,1997, available from the National Center for Biotechnology Information (NCBI), Bethesda, Md., USA and accessible through the home page of the NCBI at www.ncbi.nim.nih.gov) and FASTA (Pearson W R, Methods in Enzymology, 183, 63-99, 1990; Pearson W R and Lipman D J, Proc Nat Acad Sci USA, 85, 2444-2448,1988, available as part of the Wisconsin Sequence Analysis Package).

Preferably, the BLOSUM62 amino acid substitution matrix (Henikoff S and Henikoff J G, Proc. Nat. Acad. Sci. USA, 89, 10915-10919, 1992) is used in polypeptide sequence comparisons including where nucleotide sequences are first translated into amino acid sequences before comparison.

Preferably, the program BESTFIT is used to determine the % identity of a query polynucleotide or a polypeptide sequence with respect to a reference polynucleotide or a polypeptide sequence, the query and the reference sequence being optimally aligned and the parameters of the program set at the default value, as hereinbefore described.

"Identity Index" is a measure of sequence relatedness which may be used to compare a candidate sequence (polynucleotide or polypeptide) and a reference sequence. Thus, for instance, a candidate polynucleotide sequence having, for example, an Identity Index of 0.95 compared to a reference polynucleotide sequence is identical to the reference sequence except that the candidate polynucleotide sequence may include on average up to five differences per each 100 nucleotides of the reference sequence. Such differences are selected from the group consisting of at least one nucleotide deletion, substitution, including transition and transversion, or insertion. These differences may occur at the 5' or 3' terminal positions of the reference polynucleotide sequence or anywhere between these terminal positions, interspersed either individually among the nucleotides in the reference sequence or in one or more contiguous groups within the reference sequence. In other words, to obtain a polynucleotide sequence having an Identity Index of 0.95 compared to a reference polynucleotide sequence, an average of up to 5 in every 100 of the nucleotides of the in the reference sequence may be deleted, substituted or inserted, or any combination thereof, as hereinbefore described. The same applies mutatis mutandis for other values of the Identity Index, for instance 0.96, 0.97, 0.98 and 0.99.

Similarly, for a polypeptide, a candidate polypeptide sequence having, for example, an Identity Index of 0.95 compared to a reference polypeptide sequence is identical to the reference sequence except that the polypeptide sequence may include an average of up to five differences per each 100 amino acids of the reference sequence. Such differences are selected from the group consisting of at least one amino acid deletion, substitution, including conservative and non-conservative substitution, or insertion. These differences may occur at the amino- or carboxy-terminal positions of the reference polypeptide sequence or anywhere between these terminal positions, interspersed either individually among the amino acids in the reference sequence or in one or more contiguous groups within the reference sequence. In other words, to obtain a polypeptide sequence having an Identity Index of 0.95 compared to a reference polypeptide sequence, an average of up to 5 in every 100 of the amino acids in the reference sequence may be deleted, substituted or inserted, or any combination thereof, as hereinbefore described. The same applies mutatis mutandis for other values of the Identity Index, for instance 0.96, 0.97, 0.98 and 0.99.

The relationship between the number of nucleotide or amino acid differences and the Identity Index may be expressed in the following equation:

$$n_a \leq x_a - (x_a \cdot I),$$

in which:

$n_a$ is the number of nucleotide or amino acid differences, $x_a$ is the total number of nucleotides or amino acids in SEQ ID NO:1 or SEQ ID NO:2, respectively, I is the Identity Index, · is the symbol for the multiplication operator, and.

in which any non-integer product of $x_a$ and I is rounded down to the nearest integer prior to subtracting it from $x_a$.

"Homolog" is a generic term used in the art to indicate a polynucleotide or polypeptide sequence possessing a high degree of sequence relatedness to a reference sequence. Such relatedness may be quantified by determining the degree of identity and/or similarity between the two sequences as hereinbefore defined. Falling within this generic term are the terms "ortholog", and "paralog". "Ortholog" refers to a polynucleotide or polypeptide that is the functional equivalent of the polynucleotide or polypeptide in another species. "Paralog" refers to a polynucleotide or polypeptide that within the same species which is functionally similar.

"Fusion protein" refers to a protein encoded by two, unrelated, fused genes or fragments thereof. Examples have been disclosed in U.S. Pat. Nos. 5,541,087, 5,726,044. In the case of Fc-PHPIP-180, employing an immunoglobulin Fc region as a part of a fusion protein is advantageous for performing the functional expression of Fc-PHPIP-180 or fragments of PHPIP-180, to improve pharmacokinetic properties of such a fusion protein when used for therapy and to generate a dimeric PHPIP-180. The Fc-PHPIP-180 DNA construct comprises in 5' to 3' direction, a secretion cassette, i.e. a signal sequence that triggers export from a mammalian cell, DNA encoding an immunoglobulin Fc region fragment, as a fusion partner, and a DNA encoding PHPIP-180 or fragments thereof. In some uses it would be desirable to be able to alter the intrinsic functional properties (complement binding, Fc-Receptor binding) by mutating the functional Fc sides while leaving the rest of the fusion protein untouched or delete the Fc part completely after expression.

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

FURTHER EXAMPLES

Plasmid Constructs (All Plasmids were Verified by Sequencing)

Cloning of pDBLeu—PHP1

The cDNA encoding PHP1 was amplified by PCR using the primers Hispase-Sal-up (SEQ ID NO: 3, primer 1) and Hispase-Not-low (SEQ ID NO: 4, primer 2) and ligated into vector pCR2.1TOPO (Invitrogen). Subsequently, the vector was cleaved using Sal1 and Not1 and the PHP1-encoding fragment was ligated into pDBLeu.

Cloning of pLexA-MCS—PHP1

Oligonucleotide primer 3 Y2H-MCS1 (SEQ ID NO: 5) and primer 4 SEQ ID NO. 6 Y2H-MCS2 were annealed and ligated into EcOR1 and Sal1 restingated vector pLexA (Clontech) to generate Vector pLexA-MCS containing unique EcOR1, Sal1, Xho1 and Not1 restriction sites.

A fragment encoding PHP1 was isolated from Vector pDBLeu-PHP1 using Not1 and Sal1 and ligated into Vector pLexA-MCS to generate pLexA-MCS-PHP1. All vectors were confirmed by sequencing.

Fusionproteins

The peptide sequence of the Gal4-PHP1 fusion protein is given in SEQ ID NO: 7 comprising the Gal4 protein and a C-terminally linked full length PHP-1 protein. The corresponding peptide sequence of the LexA-PHP-1 fusion protein comprised the LexA protein sequence and a C-terminally linked full length PHP-1 protein. The sequence has been disclosed in SEQ ID NO: 8.

Yeast-Two Hybrid Screen to Select PHP1-interacting Proteins.

The yeast two-hybrid screening method is technically simple and very rapid such that several million of library clones can be screened in just a few days. All of the elements of the system are commercially available. In the screen, the His3 indicator gene will only be activated if the DNA binding domain of Gal4 (AA 1-147) and the Gal4 transactivation domain (AA 768-881) fused to the NLS of the SV40 large T antigen are brought into contact by the receptor Histidine Phosphatase and a protein ligand interaction. Although the ligands isolated from this screen bind to Histidine Phosphatase the binding partners have been confirmed in a second different—LexA-based Yeast-Two Hybrid selection scheme. If both screening procedures are implemented concurrently, ligands obtained may be tested in other systems.

A yeast Two Hybrid screen (Proquest, Life Technologies) using pDBLeu-PHP1 as bait construct and a HELA-based cDNA library as prey was performed as described (selection was performed on -Trp, -Leu, -His Minimalmedium containing 25 mM 3-Aminotriazole). Interaction was confirmed on Medium lacking Uracile, Tryptophane and Leucine as described in the manufacturers protocoll.

One positive clone representing a PHPIP-180—gene product was isolated and sequenced.

Confirmation of the PHPIP-180 ligand interaction using a LexA-based Yeast-Two Hybrid selection scheme:

To confirm the interaction in a different selection scheme, the Matchmaker LexA Two-Hybrid system (Clontech) was used due to manufacturers conditions. Vector pLexA-MCS-PHP1 was used as bait. Vector pPC86-PHPIP120, which was isolated in the Gal4 based Yeast Two Hybrid system as described above was used as prey.

Interaction of p53 and large T antigen were used as positve controls in S. cerevisiae strain EGY48-pSH18-32.

In Silico Analysis

The gene for the PHP1 ligand identified in above mentioned yeast-two-hybrid screen is located on human chromosome 1p31. The identified gene encodes a protein of 571 AA length, with no significant sequence homology to other known proteins. While partial sequences of this gene and their corresponding virtual ORF predictions have already been deposited in the databank a protein function as revealed in this study has not been described previously.

We claim:

1. An isolated 180 Kd protein histidine phosphatase interacting protein (PHPIP-180) polypeptide which is:
   (a) an isolated polypeptide encoded by a polynucleotide consisting of the nucleotide sequence of SEQ ID NO: 1; or
   (b) an isolated polypeptide consisting of the polypeptide of SEQ ID NO:2,
wherein each of said PHPIP-180 polypeptides of (a) to (b) has the ability to bind specifically to protein histidine phosphatase-1 (PHP 1) polypeptide having the amino acid sequence of SEQ ID NO:7.

2. The isolated polypeptide of claim 1 which consists of the polypeptide sequence of SEQ ID NO: 2.

3. A fusion protein comprising an immunoglobulin Fc-region and the polypeptide of claim 1.

4. An isolated polypeptide which consists of the polypeptide sequence of SEQ NO:2, wherein said polypeptide has the ability to bind specifically to protein histidine phosphatase-1 (PHP1) polypeptide having the amino acid sequence of SEQ ID NO:7.

* * * * *